United States Patent
Woo et al.

(10) Patent No.: US 10,479,763 B2
(45) Date of Patent: Nov. 19, 2019

(54) CHIRAL RESOLUTION METHOD OF N-[4-(1-AMINOETHYL)-PHENYL]-SULFONAMIDE DERIVATIVES

(71) Applicant: AMOREPACIFIC CORPORATION, Seoul (KR)

(72) Inventors: Byoung Young Woo, Yongin-si (KR); Ki-Wha Lee, Yongin-si (KR); Kwang-Hyun Shin, Yongin-si (KR); Miyoung Park, Yongin-si (KR); Kyoungmi Jung, Yongin-si (KR); Joonho Choi, Yongin-si (KR); Gyeyoung Choi, Yongin-si (KR); Wonkyung Cho, Yongin-si (KR); Young-Ho Park, Yongin-si (KR)

(73) Assignee: AMOREPACIFIC CORPORATION, Seoul (KR)

( * ) Notice: Subject to any disclaimer, the term of this patent is extended or adjusted under 35 U.S.C. 154(b) by 0 days.

(21) Appl. No.: 15/325,349

(22) PCT Filed: Feb. 15, 2016

(86) PCT No.: PCT/KR2016/001474
§ 371 (c)(1),
(2) Date: Jan. 10, 2017

(87) PCT Pub. No.: WO2016/133317
PCT Pub. Date: Aug. 25, 2016

(65) Prior Publication Data
US 2017/0342027 A1   Nov. 30, 2017

(30) Foreign Application Priority Data

Feb. 17, 2015 (KR) .......................... 10-2015-0024334
Jun. 30, 2015 (EP) ....................................... 15174617

(51) Int. Cl.
| | | |
|---|---|---|
| C07C 303/42 | (2006.01) | |
| C07C 303/36 | (2006.01) | |
| C07C 311/08 | (2006.01) | |
| C07C 303/44 | (2006.01) | |
| C07D 213/56 | (2006.01) | |
| C07B 57/00 | (2006.01) | |
| C07C 63/06 | (2006.01) | |

(52) U.S. Cl.
CPC ............ *C07C 303/42* (2013.01); *C07B 57/00* (2013.01); *C07C 63/06* (2013.01); *C07C 303/36* (2013.01); *C07C 303/44* (2013.01); *C07C 311/08* (2013.01); *C07D 213/56* (2013.01); *C07B 2200/07* (2013.01)

(58) Field of Classification Search
None
See application file for complete search history.

(56) References Cited

U.S. PATENT DOCUMENTS

| | | |
|---|---|---|
| 4,968,837 A | 11/1990 | Manimaran et al. |
| 5,387,695 A | 2/1995 | Lee et al. |
| 6,265,615 B1 | 7/2001 | Kaner et al. |
| 2003/0073719 A1 | 4/2003 | Wilcox et al. |
| 2006/0122429 A1 | 6/2006 | Ditrich et al. |
| 2006/0211741 A1 | 9/2006 | Hanazawa et al. |
| 2008/0312234 A1 | 12/2008 | Kim et al. |
| 2012/0041225 A1* | 2/2012 | Vaidya .................... C07B 57/00 560/78 |

FOREIGN PATENT DOCUMENTS

| | | |
|---|---|---|
| JP | S60152425 | 8/1985 |
| JP | 2012508219 | 4/2012 |
| KR | 1020020051937 | 6/2002 |
| KR | 1020080002931 | 1/2008 |
| KR | 1020090033916 | 4/2009 |
| KR | 1020160101554 | 8/2016 |
| WO | 2007129188 | 11/2007 |
| WO | 2007133637 | 11/2007 |
| WO | 2008013414 | 1/2008 |
| WO | 2010010934 | 1/2010 |
| WO | 2010052475 | 5/2010 |

OTHER PUBLICATIONS

Extended European Search Report—European Application No. EP16752647.4 dated Dec. 1, 2017—references cited within.
Korean Office Action—Korean Application No. 10-2017-7000413 dated May 19, 2017, citing reference listed within.
International Search Report—PCT/KR2016/001474 dated May 20, 2016.
Written Opinion—PCT/KR2016/001474 dated May 20, 2016.
Takashi Nakamura et al., "Optical Resolution of Imidazole Compound by Preferential Dissolution Method", A Collection of Chemical Engineering Papers, 1997, vol. 23, No. 5, pp. 618-623.

(Continued)

*Primary Examiner* — Sudhakar Katakam
*Assistant Examiner* — Jennifer C Sawyer
(74) *Attorney, Agent, or Firm* — Cantor Colburn LLP

(57) ABSTRACT

The present specification relates to a chiral resolution method of a stereoisomer mixture, comprising a step of mixing a stereoisomer mixture of compounds, in which an amine group is bound to an asymmetric carbon atom, with a chiral auxiliary and salt-forming auxiliary compound, wherein the chiral auxiliary is an O,O'-diacyltartaric acid derivative, more specifically, a 2,3-dibenzoyl-tartaric acid or O,O'-di-p-toluoyl tartaric acid, the salt-forming auxiliary compound is mandelic acid or camphorsulfonic acid, and an optical isomer having a high level of optical purity can be obtained by using the method. Therefore, according to one aspect of the present invention, the method can be useful in pharmaceutical or cosmetic field when preparing an optical isomer having a high optical purity.

22 Claims, No Drawings

(56) References Cited

OTHER PUBLICATIONS

Yuji Omichi et al,, "Optical Resolution of DL-Mandelic Acid by Preferential Crystallization Procedure", Bulletin of the Chemical Society of Japan, 1979, No. 8, pp. 1092-1096.
Japanese Office Action-Japanese Application No. 2017-502582 dated Sep. 3, 2019, citing references listed within.

* cited by examiner

CHIRAL RESOLUTION METHOD OF N-[4-(1-AMINOETHYL)-PHENYL]-SULFONAMIDE DERIVATIVES

TECHNICAL FIELD

The present disclosure relates to a method for chiral resolution of N-[4-(1-aminoethyl)-phenyl]-sulfonamide derivatives.

BACKGROUND ART

Recently, demand on stereochemically pure compounds is increasing rapidly. One important use of these pure stereoisomers is as synthetic intermediates in the pharmaceutical industry. For example, it is becoming gradually evident that enantiopure drugs possess many advantages over racemic drug mixtures. The advantages often include less side effects and better efficacies of the enantiopure compounds [see, e.g., Stinson, S.C., Chem Eng News, Sep. 28, 1992, pp. 46-79].

For example, triadimenol can exist as four isomers. The (−)-(1S,2R)-isomer has a stronger activity than the (+)-(1R,2R)-isomer and the (−)-(1S,2S)-isomer has a stronger activity than the (+)-(1R,2S)-isomer. Among the four isomers of dichlorobutrazol, the (1R,2R)-isomer is known to have stronger activity. Also, for etaconazole, the (+)-(2S,4S)- and (−)-(2S,4R)-isomers are known to have better fungicidal effect than others.

Therefore, if only one isomer having higher activity can be prepared selectively, better effect can be achieved with less amount and, accordingly, environmental pollution resulting from the use of the chemicals can be decreased. Especially for drugs, if one of the isomers exhibits toxicity in human, it is very important to selectively prepare one isomer only.

Accordingly, in medicine-, pharmacy- and biochemistry-related fields, preparation of optically pure compounds for improving medicinal effect or preventing side effects is a very important task.

However, still many drugs are used as racemic compounds with unavoidable side effects owing to the existence of undesirable enantiomers (see, e.g., Nguyen, et al., Chiral Drugs: An Overview, Int. J. Biomed. Sci., 2 (2006) 85-100). A few techniques are available for the preparative or analytical scale chiral separations. However, it costs immense time and efforts to find out a separation technique suited for the racemates of interest. Even if one should succeed in resolving an enantiomer, he will then face the next difficulty, i.e., to enable the chiral resolution on an industrial scale.

For example, the efficacies of pure stereoisomers of vanilloid antagonists including N-[4-(1-aminoethyl)-phenyl]-sulfonamide derivatives have been elucidated [e.g., WO 2008-013414 A1, WO 2007-133637 A2, WO 2007-129188 A1, WO 2010-010934 A1].

As a method for synthesizing single isomers of the N-[4-(1-aminoethyl)-phenyl]-sulfonamide derivatives, asymmetric synthesis using the Ellman's reagent is known. For example, WO 2008-013414 A1, WO 2007-133637 A2, WO 2007-129188 A1 and WO 2010-010934 A1 present a method of obtaining desired stereoisomers by introducing the Ellman's reagent and inducing asymmetric reduction using the same. However, this method is disadvantageous in that a low-temperature reaction condition should be maintained to achieve high optical purity (enantiomer excess, % ee). Also, the process is dangerous because excessive generation of hydrogen and heat occurs when the reaction is terminated. In addition, the disposal cost of the excessively produced organic and inorganic wastes is also disadvantageous in terms of economy.

DISCLOSURE

Technical Problem

Although asymmetric synthesis of N-[4-(1-aminoethyl)-phenyl]-sulfonamide derivatives has been reported, a preparation method that can be utilized in commercial scale has not been established as yet because of the problems in economy and safety.

Accordingly, the present disclosure is directed to solving the problems of the existing asymmetric synthesis method and providing a novel method for chiral resolution of a mixture of stereoisomers to an S or R compound having high optical purity.

Technical Solution

In an aspect, the present disclosure provides a method for resolving N-[4-(1-aminoethyl)-phenyl]-sulfonamide derivatives of formula (I):

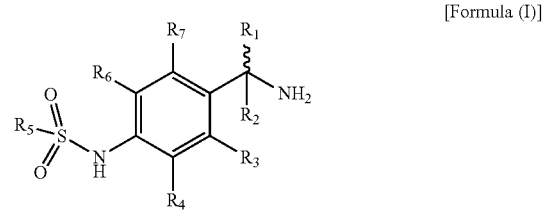

[Formula (I)]

to the respective compounds with high optical purity by using an O,O'-diacyltartaric acid derivative (an example of chiral auxiliaries) and a soluble salt-forming acid (an example of salt-forming compounds). In one embodiment, the present disclosure relates to a method for resolving (R,S)—N-[4-(1-aminoethyl)-phenyl]-sulfonamide to N-[4-(1-aminoethyl)-phenyl]-sulfonamide having high optical purity, including: (i) mixing an (R,S)—N-[4-(1-aminoethyl)-phenyl]-sulfonamide derivative with an optically active O,O'-diacyltartaric acid derivative (an example of chiral auxiliaries) and a soluble salt-forming acid (an example of salt-forming compounds) in a polar protic solvent, and thereby preparing an (R)— or (S)—N-[4-(1-aminoethyl)-phenyl]-sulfonamide diacyltartrate salt or a solvate thereof with high optical purity, and (ii) liberating the resulting N-[4-(1-aminoethyl)-phenyl]-sulfonamide salt or a solvate thereof with high optical purity by using a base.

According to the method of the present disclosure, N-[4-(1-aminoethyl)-phenyl]-sulfonamide derivatives can be easily resolved to the respective compounds having high optical purity.

N-[4-(1-aminoethyl)-2,6-difluorophenyl]-methanesulfonamide is a general name of a compound which has a structure of formula (II) as follows:

[Formula (II)]

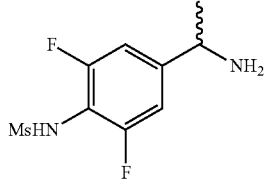

and it is known as a useful intermediate product for manufacturing a compound acting as a TRPV1 (transient receptor potential cation channel subfamily V member 1, or capsaicin receptor or vanilloid receptor 1) antagonist.

As can be seen in formula (II), N-[4-(1-aminoethyl)-2,6-difluorophenyl]-methanesulfonamide is a chiral compound wherein an amine group is bonded to an asymmetric carbon atom (chiral center).

Advantageous Effects

In accordance with a method for chiral resolution according to an aspect of the present disclosure, a mixture of stereoisomers, particularly a mixture of stereoisomers of a compound wherein an amine group is bonded to an asymmetric carbon atom, can be chirally resolved easily to a compound having high optical purity. This synthesis method provides improved safety and economy over the asymmetric synthesis method using the Ellman's reagent. It allows for chiral resolution with comparable or better optical purity and provides improved economy and environment friendliness through collection and recycling of salts. Accordingly, this method can be advantageously used in pharmaceutical and cosmetic fields where chiral resolution of compounds is desired.

In particular, the method according to the present disclosure allows for effective preparation of desired stereoisomers with comparable or better optical purity as compared to the existing asymmetric synthesis method using Ellman's reagent. It is also effective for large-scale production and provides economic advantages.

DETAILED DESCRIPTION OF INVENTION

In one aspect, the present disclosure provides a method for resolution of a mixture of stereoisomers of compound, comprising a step of mixing said mixture of stereoisomers of compound with
(i) a chiral auxiliary and
(ii) an auxiliary salt-forming compound
in the presence of a solvent, thereby precipitating a diastereomeric salt of said chiral auxiliary (i) with the compound. In one aspect, the method for resolution is related to a method for chiral resolution.

In one aspect, the present disclosure provides a method for resolving a mixture of stereoisomers of compound of formula (I),

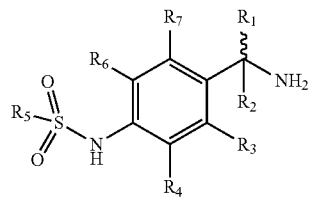

comprising a step of mixing said mixture of stereoisomers of the compound of formula (I) with
(i) a chiral auxiliary and
(ii) an auxiliary salt-forming compound
in the presence of a solvent, thereby precipitating a diastereomeric salt of said chiral auxiliary (i) with the compound of formula (I).

In an embodiment of the present disclosure, a method according to the present invention provides a stereoisomer of the compound of formula (I) in enantiomeric excess, specifically with high optical purity.

The term "in enantiomeric excess" in the present disclosure generally includes any increase in the ratio of enantiomers, thus not only an enantiomeric excess compared to a racemic mixture, but also an increase of one enantiomer over another compared to a mixture wherein the ratio of enantiomers is not 1:1 (as in a racemate). In some embodiments, the term in enantiomeric excess specifically corresponds to an enantiomeric excess value ("% ee") of at least 80%, or at least 90%, or at least 95% or at least 96%, or at least 97%, or at least 98%, or at least 99%.

The term "high optical purity" in the present disclosure is a term well-understood in the art. In some embodiments, the term "high optical purity" corresponds to an enantiomeric excess value ("% ee") of at least 80%, or at least 90%, or at least 95% or at least 96%, or at least 97% or at least 98% or at least 99%.

In an aspect, the present disclosure provides a method for chiral resolution of a mixture of stereoisomers, including mixing a mixture of stereoisomers with a soluble salt-forming acid (an example of salt-forming compounds), and an optically active 0,0'-diacyltartaric acid derivative (an example of chiral auxiliaries).

The term 'salt-forming compound' in the present disclosure is not only a compound to resolve a mixture of stereoisomers, but also a compound to help to increase optical purity of the mixture of stereoisomers. The different solubility of the salt formed with an enantiomer and a chiral auxiliary in the salt-forming compound is used to help resolving the mixture of stereoisomers. A salt-forming compound may be an acid or a salt thereof which are able to solubilize the mixture of stereoisomers to be resolved. This salt-forming compound helps one enantiomer which does not form an insoluble salt with the chiral auxiliary to remain soluble, thereby helping to obtaining a non-soluble salt of another enantiomer in enantiomeric excess.

In an exemplary embodiment of the present disclosure, the soluble salt-forming acid (an example of salt-forming compounds) may be selected from a group comprising mandelic acid, camphorsulfonic acid, a stereoisomer thereof, and a combination thereof. The term 'chiral auxiliary' in the present disclosure is well recognized by a person skilled in the art and specifically means a chemical compound or unit that is temporarily incorporated into an organic synthesis to control the stereochemical outcome of the synthesis. The chirality of the chiral auxiliary can bias the stereoselectivity of one or more subsequent reactions (see, e.g., chiral auxiliary, Wikipedia: http://en.wikipedia.org/wiki/Chiral_auxiliary). In the present disclosure, the terms chiral auxiliary and chiral acid may be used interchangeably.

In an exemplary embodiment of the present disclosure, the chiral auxiliary may be an O,O'-diacyltartaric acid derivative. The chiral auxiliary may be selected from a group consisting of 2,3-dibenzoyltartaric acid, O,O'-di-p-toluoyltartaric acid, a stereoisomer thereof, and a combination thereof.

In an exemplary embodiment of the present disclosure, the 2,3-dibenzoyltartaric acid may be (+)-2,3-dibenzoyl-D-tartaric acid or (−)-2,3-dibenzoyl-L-tartaric acid, which are optical isomers of each other, and the O,O'-di-p-toluoyltartaric acid may be (+)-O,O'-di-p-toluoyl-D-tartaric acid or (−)-O,O'-di-p-toluoyl-L-tartaric acid, which are optical isomers of each other. Although the D and L forms of the tartaric acid derivative may be used either alone or in combination, it is preferred that they are used alone without being mixed with each other. When the D and L forms of the tartaric acid derivative are used in combination in the method according to the present disclosure, a lower optical purity may be obtained as compared to when the D or L form is used alone.

In an exemplary embodiment of the present disclosure, the mandelic acid may be D-mandelic acid or L-mandelic acid, which are optical isomers of each other, or a combination thereof, and the camphorsulfonic acid may be (1R)-(−)-10-camphorsulfonic acid or (1S)-(+)-10-camphorsulfonic acid, which are optical isomers of each other, or a combination thereof. As demonstrated in the Examples, the optical isomer form of the mandelic acid or the camphorsulfonic acid has an insignificant effect on the optical isomer form of the final product and the final product of high optical purity can be obtained when the optical isomers of the mandelic acid or the camphorsulfonic acid are used either alone or in combination.

In an exemplary embodiment of the present disclosure, the mixture of stereoisomers may be a mixture of stereoisomers of a compound having an asymmetric carbon atom. Specifically, in an exemplary embodiment of the present disclosure, the compound having an asymmetric carbon atom may be one wherein an amine group is bonded thereto. Specifically, in an exemplary embodiment of the present disclosure, the compound may have, in addition to the amine group, a substituted or unsubstituted phenyl group bonded to the asymmetric carbon atom. More specifically, in an exemplary embodiment of the present disclosure, the compound having an asymmetric carbon atom may be a compound of formula (I).

In an exemplary embodiment of the present disclosure, an R or S optical isomer with high optical purity may be obtained from the mixture of stereoisomers.

In an exemplary embodiment of the present disclosure, when the chiral auxiliary is selected from a group comprising (+)-2,3-dibenzoyl-D-tartaric acid and (+)-O,O'-di-p-toluoyl-D-tartaric acid, and a combination thereof, an R enantiomer may be obtained in high enantiomeric excess.

In an exemplary embodiment of the present disclosure, when the chiral auxiliary is selected from a group comprising (−)-2,3-dibenzoyl-L-tartaric acid or (−)-O,O'-di-p-toluoyl-L-tartaric acid, and a combination thereof, an S enantiomer may be obtained in high enantiomeric excess.

In an exemplary embodiment of the present invention, the salt-forming compound may be D-mandelic acid, L-mandelic acid, (1R)-(−)-10-camphorsulfonic acid or (1S)-(+)-10-camphorsulfonic acid, or a combination thereof.

In an exemplary embodiment of the present disclosure, the compound wherein an amine group is bonded to an asymmetric carbon atom may have a structure of formula (I):

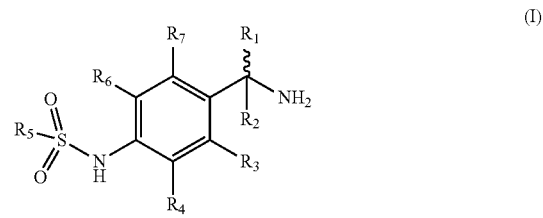

wherein
each of $R_1$, $R_2$, $R_3$, $R_4$, $R_5$, $R_6$ and $R_7$ is independently any one selected from a group consisting of H, —$NH_2$, a $C_{1-6}$ alkyl group, a $C_{2-6}$ alkenyl group, a $C_{2-6}$ alkynyl group and a halogen, and $R_1$ and $R_2$ are different from each other.

In an exemplary embodiment of the present disclosure, the halogen may be at least one selected from a group consisting of F, Cl, Br, and I, specifically from a group consisting of F and Cl.

In an exemplary embodiment of the present disclosure, the $R_1$ may be one selected from a group consisting of a methyl group, an ethyl group, a propyl group, a butyl group and a pentyl group, and the $R_2$ may be hydrogen.

In an exemplary embodiment of the present disclosure, the $R_1$ may be a methyl group, the $R_3$ and the $R_7$ may be hydrogen, and each of the $R_4$, the $R_5$ and the $R_6$ may independently be one selected from a group consisting of F, Cl, Br, I and a $C_{1-6}$ alkyl group.

In an exemplary embodiment of the present disclosure, the $R_4$ and the $R_6$ may be F, and the $R_5$ may be a methyl group.

In an exemplary embodiment of the present disclosure, the compound may be N-{4-[(1R/S)-1-aminoethyl]-2,6-difluorophenyl}methanesulfonamide.

In an exemplary embodiment of the present disclosure, the solvent may be added at an amount to achieve complete dissolution of all reactants.

In an exemplary embodiment of the present disclosure, the solvent may be a polar protic solvent.

In an exemplary embodiment of the present disclosure, the polar protic solvent may be one or more selected from a group consisting of water, a $C_{1-14}$ alcohol, isopropyl alcohol, acetic acid, nitromethane, propionic acid, formic acid and combinations thereof. Specifically, the polar protic solvent may be one or more selected from a group consisting of water, methanol, ethanol and isopropyl alcohol. More specifically, the polar protic solvent may be methanol or isopropyl alcohol. More specifically, the polar protic solvent may be isopropyl alcohol.

In an exemplary embodiment of the present disclosure, the polar protic solvent may be used in an amount of 5-15 times, specifically 7-13 times, more specifically 9-11 times, more specifically 10 times, based on the total weight of the mixture of stereoisomers (i.e. volume [solvent]/weight [stereoisomers], or (v/w)).

In an exemplary embodiment of the present disclosure, the mixing may be performed at 40-70° C. or at the boiling point of the solvent or solvent mixture. The mixing may be performed for 1-4 hours. In an exemplary embodiment of the present disclosure, the mixing may be performed by stirring under reflux.

In an exemplary embodiment of the present disclosure, the mixing may be performed at a temperature of at least 30° C., at least 40° C., more specifically at least 50° C., or at the boiling point of the solvent or solvent mixture.

In an exemplary embodiment of the present disclosure, the mixing temperature may be 30° C. or higher, 40° C. or higher, 50° C. or higher, 60° C. or higher or 70° C. or higher, or 70° C. or lower, 60° C. or lower, 50° C. or lower, 40° C. or lower or 30° C. or lower. The mixing temperature may be specifically 40-60° C., more specifically 45-55° C., more specifically 50° C.

In an exemplary embodiment of the present disclosure, the mixing time may be 1 hour or longer, 2 hours or longer, 3 hours or longer, 4 hours or longer or 5 hours or longer, or 6 hours or shorter, 5 hours or shorter, 4 hours or shorter, 3 hours or shorter, 2 hours or shorter or 1 hour or shorter. The mixing time may be specifically 2-4 hours, more specifically mixing time 2.5-3.5 hours, more specifically 3 hours.

In an exemplary embodiment of the present disclosure, the method may be performed by reacting at a ratio of two molar equivalents of the compound having a structure of formula (I) (comprising the R and S optical isomers in a given ratio) per one molar equivalent of the chiral auxiliary. In an exemplary embodiment of the present disclosure, the reacting may be performed according to Scheme 1.

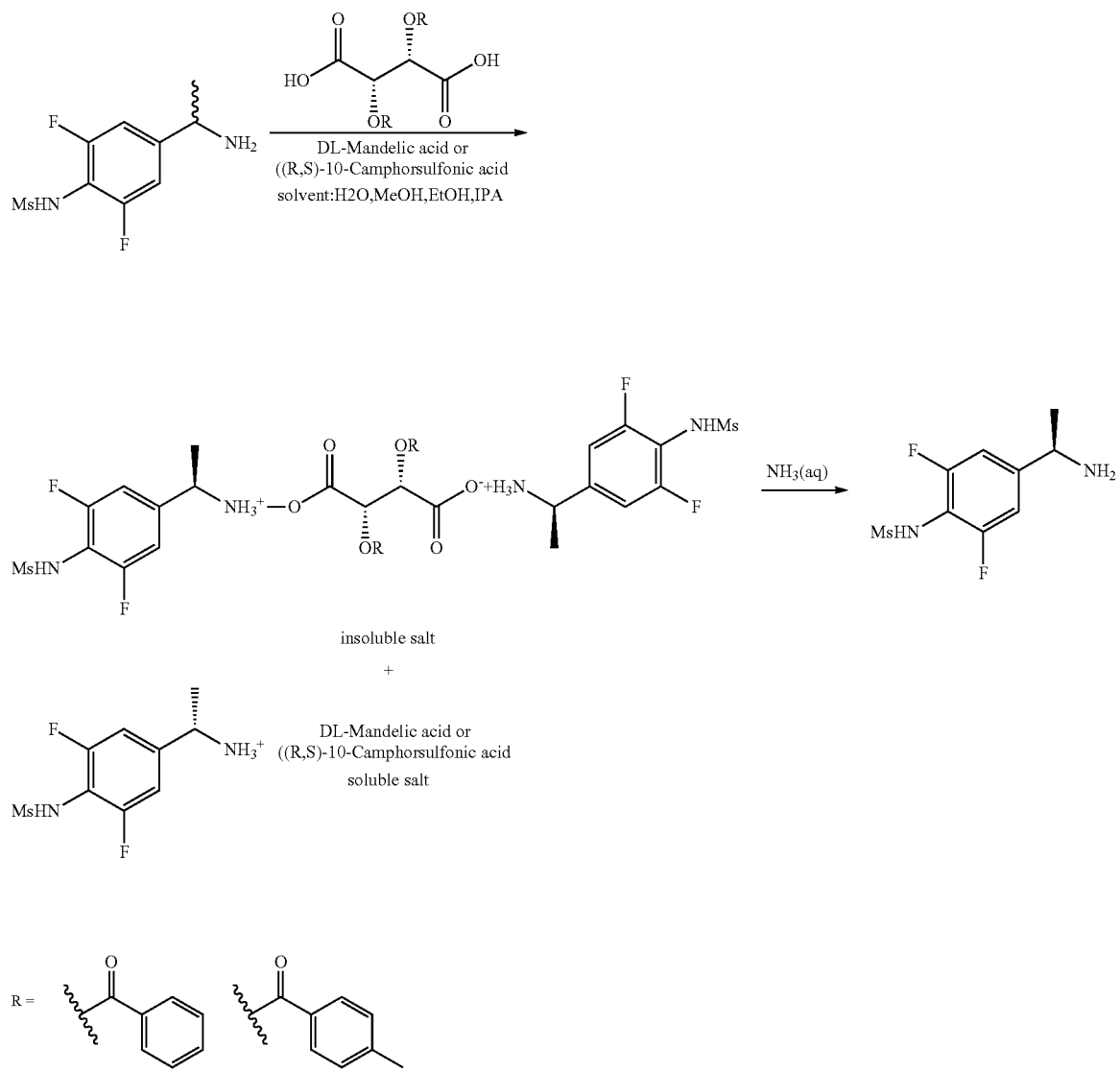

According to Scheme 1, two molecules of the compound of formula (I) which has one optical activity are bound to one molecule of the chiral auxiliary to form an insoluble salt, which can be precipitated. In contrast, the compound remaining unbound to the chiral auxiliary is dissolved in the salt-forming compound and thus is not precipitated. Through this reaction, the method according to the present disclosure can resolve a compound having high optical purity from the mixture of stereoisomers. On the other hand, if one molecule of the compound of formula (I) is bound to one molecule of the chiral auxiliary to form a salt, the chiral resolution desired by the present disclosure is not so good as compared to when two molecules are bound.

In an exemplary embodiment of the present disclosure, the molar equivalent of the chiral auxiliary to the mixture of stereoisomers may be a molar equivalent for reacting two molecules of the R- or S-form of the compound having a structure of formula (I) with one molecule of the chiral auxiliary.

In an exemplary embodiment of the present disclosure, the molar equivalent ratio of the chiral auxiliary to 1 molar equivalent of the mixture of stereoisomers may be equal to or less than 0.5, 0.10-0.5, 0.15-0.5, 0.25-0.35, or 0.25.

In an exemplary embodiment of the present disclosure, the chiral auxiliary may be used in an amount of 0.01 equivalent or more, 0.05 equivalent or more, 0.10 equivalent or more, 0.15 equivalent or more, 0.2 equivalent or more, 0.25 equivalent or more, 0.3 equivalent or more, 0.35 equivalent or more, 0.4 equivalent or more, 0.45 equivalent or more, 0.5 equivalent or more, 0.55 equivalent or more or 0.6 equivalent or more, or 0.6 equivalent or less, 0.55 equivalent or less, 0.5 equivalent or less, 0.45 equivalent or less, 0.4 equivalent or less, 0.35 equivalent or less, 0.3 equivalent or less, 0.25 equivalent or less, 0.2 equivalent or less, 0.15 equivalent or less, 0.10 equivalent or less, 0.05 equivalent or less or 0.01 equivalent or less per 1 equivalent of the mixture of stereoisomers.

In an exemplary embodiment of the present disclosure, the molar equivalent ratio of the salt-forming compound to 1 molar equivalent of the mixture of stereoisomers may be 0.50-1.5, 0.75-1.5, or 0.75-1.0.

Specifically, the salt-forming compound may be used in an amount of 0.5 equivalent or more, 0.55 equivalent or more, 0.6 equivalent or more, 0.65 equivalent or more, 0.7 equivalent or more, 0.75 equivalent or more, 0.8 equivalent or more, 0.85 equivalent or more, 0.9 equivalent or more, 0.95 equivalent or more, 1.0 equivalent or more, 1.05 equivalents or more, 1.1 equivalents or more, 1.15 equivalents or more, 1.2 equivalents or more, 1.25 equivalents or more, 1.3 equivalents or more, 1.35 equivalents or more, 1.4 equivalents or more, 1.45 equivalents or more, 1.5 equivalents or more, 1.55 equivalents or more or 1.6 equivalents or more, or 1.6 equivalents or less, 1.55 equivalents or less, 1.5 equivalents or less, 1.45 equivalents or less, 1.4 equivalents or less, 1.35 equivalents or less, 1.3 equivalents or less, 1.25 equivalents or less, 1.2 equivalents or less, 1.15 equivalents or less, 1.1 equivalents or less, 1.05 equivalents or less, 1.0 equivalent or less, 0.95 equivalent or less, 0.9 equivalent or less, 0.85 equivalent or less, 0.8 equivalent or less, 0.75 equivalent or less, 0.7 equivalent or less, 0.65 equivalent or less, 0.6 equivalent or less, 0.55 equivalent or less, or 0.50 equivalent or less per 1 equivalent of the mixture of stereoisomers.

In an exemplary embodiment of the present disclosure, the molar equivalent ratio of the chiral auxiliary and the salt-forming compound together to 1 molar equivalent of the mixture of stereoisomers may be 0.6-2.0, 0.75-2.0, 0.8-2.0, 1.0-1.85, or 1.0-1.35. Specifically, such molar equivalent ratio of the chiral auxiliary and the salt-forming compound together may be a value that sums the molar equivalent of the chiral auxiliary and the molar equivalent of the salt-forming compound described above.

In an exemplary embodiment of the present disclosure, when the salt-forming compound and the chiral auxiliary are used in combination, a higher optical purity may be obtained when the chiral auxiliary is used at a smaller equivalent ratio than the salt-forming compound per 1 equivalent of the racemic mixture.

In an exemplary embodiment of the present disclosure, a stereoisomer of the compound with at least 96%, at least 97%, at least 98%, at least 99%, or 96% to 99% enantiomeric excess obtained by a method according to the present invention is provided. In another aspect, the present disclosure provides an R or S optical isomer compound prepared by resolving a mixture of stereoisomers by the method according to the present disclosure.

In an exemplary embodiment of the present disclosure, the stereoisomer may be N-{4-[(1R)-1-aminoethyl]-2,6-difluorophenyl}methanesulfonamide or N-{4-[(1 S)-1-aminoethyl]-2,6-difluorophenyl}methanesulfonamide.

In the context of the present disclosure, an asymmetric carbon atom may refer to a carbon atom that is attached to four different types of atoms, radicals or functional groups. A compound having an asymmetric carbon atom exhibits optical rotation, optical activity, or optical isomerism.

In the context of the present disclosure, a mixture of stereoisomers may refer to a mixture of two enantiomers having optical activity. The mixing ratio may be 1:1 (corresponding to a racemic mixture) or, more generally, any ratio ranging from 1:10 to 10:1. In the context of the present disclosure, the mixture of stereoisomers may be an artificially synthesized one or a mixture with an unknown ratio of an R optical isomer to an S optical isomer. In accordance with the method of the present disclosure, the ratio of one of the R or S optical isomers can be increased remarkably and the desired optical isomer can be obtained with high optical purity regardless of the mixing ratio of the mixture. Specifically, the mixture of stereoisomers to be resolved may be a 1:1 mixture of R and S optical isomers.

In the context of the present disclosure, N-[4-(1-aminoethyl)-2,6-difluorophenyl]-methanesulfonamide refers to a compound of CAS No. 1202743-51-8 with a molecular weight of 250.27 Da. It may be used interchangeably with INT-2 in the present disclosure. It may also be a mixture of stereoisomers wherein R and S optical isomers are mixed.

In the context of the present disclosure, N-{4-[(1R)-1-aminoethyl]-2,6-difluorophenyl}methanesulfonamide hydrochloride refers to a compound of CAS No. 956901-23-8 with a molecular weight of 286.73 Da and N-{4-[(1R)-1-aminoethyl]-2,6-difluorophenyl}methanesulfonamide refers to a compound of CAS No. 957103-01-4. In the present disclosure, N-{4-[(1R)-1-aminoethyl]-2,6-difluorophenyl}methanesulfonamide may be used interchangeably with an R isomer of INT-3.

In the context of the present disclosure, 3-(2-propyl-6-trifluoromethylpyridin-3-yl)-acrylic acid refers to a compound of CAS No. 1005174-17-3 with a molecular weight of 259.22 Da.

In the context of the present disclosure, (R)—N-[1-(3,5-difluoro-4-methanesulfonylaminophenyl)-ethyl]-3-(2-propyl-6-trifluoromethylpyridin-3-yl)-acrylamide (PAC-14028) refers to a compound of CAS No. 1005168-10-4 with a molecular weight of 491.47 Da.

In an exemplary embodiment of the present disclosure, the R or S optical isomer of INT-3 may be obtained by a method including:

mixing INT-2 (N-[4-(1-aminoethyl)-2,6-difluorophenyl]-methanesulfonamide) with the chiral auxiliary and the salt-forming compound;

adding to the mixture a polar protic solvent of 10 times based on the weight of the INT-2 (v/w);

stirring the resulting mixture solution with the polar protic solvent added at 30-70° C. for 1-4 hours under reflux;

cooling the mixture; and obtaining a chiral acid salt of INT-3 by filtering the resulting solid.

In an exemplary embodiment of the present disclosure, the cooling may performed at 15-30° C. after the stirring under reflux.

In an exemplary embodiment of the present disclosure, the cooling may be performed at a temperature of 10° C. or higher, 15° C. or higher, 20° C. or higher, 22° C. or higher, 24° C. or higher, 25° C. or higher, 26° C. or higher, 28° C. or higher, 30° C. or higher or 35° C. or higher, or 40° C. or lower, 35° C. or lower, 30° C. or lower, 28° C. or lower, 26° C. or lower, 25° C. or lower, 24° C. or lower, 22° C. or lower, 20° C. or lower, 15° C. or lower, 10° C. or lower or 5° C. or lower.

In an exemplary embodiment of the present disclosure, the method may further include a step of separating the chiral acid from the obtained chiral acid salt of INT-3. Specifically, the separation may be performed by adding to the chiral acid salt of INT-3 water (5 times based on its weight) and 2 equivalents of a 28 vol % ammonia aqueous solution, obtaining a suspension by stirring for 20-50 minutes, filtering the suspension and obtaining an R or S optical isomer of INT-3 by removing excess water under reduced pressure.

In another aspect, the present disclosure provides a method for chiral resolution of a mixture of stereoisomers, including:

(1) a step of mixing a mixture of stereoisomers of a compound wherein an amine group is bonded to an asymmetric carbon atom with a chiral auxiliary and a salt-forming compound.

In an exemplary embodiment of the present disclosure, the compound may be N-{4-[(1R/S)-1-aminoethyl]-2,6-difluorophenyl}methanesulfonamide.

In an exemplary embodiment of the present disclosure, the chiral auxiliary in the step (1) may be at least one selected from a group consisting of 2,3-dibenzoyltartaric acid, O,O'-di-p-toluoyltartaric acid, stereoisomers thereof and a combination thereof.

In an exemplary embodiment of the present disclosure, the salt-forming compound in the step (1) may be at least one selected from a group consisting of mandelic acid, camphorsulfonic acid, stereoisomers thereof and a combination thereof.

In an exemplary embodiment of the present disclosure, the method may further include, after the step (1): (2) a step of adding a solvent to the mixture of the step (1).

In an exemplary embodiment of the present disclosure, the solvent may be a polar protic solvent.

In an exemplary embodiment of the present disclosure, the method may further include: (3) a step of stirring the resulting mixture solution under reflux.

In an exemplary embodiment of the present disclosure, the stirring in the step (3) may be performed for 30 minutes or longer, 1 hour or longer, 1.5 hours or longer, 2 hours or longer, 2.5 hours or longer, 3 hours or longer, 3.5 minutes or longer or 4 hours or longer, or for 5 hours or shorter, 4.5 hours or shorter, 4 hours or shorter, 3.5 hours or shorter, 3 hours or shorter, 3.5 hours or shorter, 3 hours or shorter, 2.5 hours or shorter, 2 hours or shorter, 1.5 hours or shorter, 1 hour or shorter or 30 minutes or shorter.

In an exemplary embodiment of the present disclosure, the stirring in the step (3) may be performed at 20° C. or higher, 25° C. or higher, 30° C. or higher, 35° C. or higher, 40° C. or higher, 45° C. or higher, 50° C. or higher, 55° C. or higher or 60° C. or higher, or at 70° C. or lower, 65° C. or lower, 60° C. or lower, 55° C. or lower, 50° C. or lower, 45° C. or lower, 40° C. or lower, 35° C. or lower, 30° C. or lower, 25° C. or lower or 20° C. or lower.

In an exemplary embodiment of the present disclosure, the method may further include: (4) a step of cooling the mixture of the step (3).

In an exemplary embodiment of the present disclosure, the method may further include: (5) a step of obtaining a diastereomer salt of the compound by filtering the resulting solid. Specifically, in an exemplary embodiment of the present disclosure, the diastereomer salt of the compound may be a diastereomer salt of INT-3.

In an exemplary embodiment of the present disclosure, the method may further include: (6) a step of removing or separating a chiral acid from the obtained diastereomer salt.

In an exemplary embodiment of the present disclosure, the step (6) may include: 1) a step of adding to the diastereomer salt of INT-3 water and an ammonia aqueous solution. Specifically, in an exemplary embodiment of the present disclosure, the water in the step (6) may be used in an amount of 2 times or more, 3 times or more, 4 times or more, 5 times or more, 6 times or more or 7 times or more, or 7 times or less, 6 times or less, 5 times or less, 4 times or less, 3 times or less or 2 times or less, based on the weight of the diastereomer salt of INT-3. Specifically, in an exemplary embodiment of the present disclosure, the ammonia aqueous solution in the step (6) may be a 20 vol % or higher, 24 vol % or higher, 28 vol % or higher, 32 vol % or higher, 36 vol % or higher or 40 vol % or higher ammonia aqueous solution, or a 40 vol % or lower, 36 vol % or lower, 32 vol % or lower, 28 vol % or lower, 24 vol % or lower or 20 vol % or lower ammonia aqueous solution. Specifically, in an exemplary embodiment of the present disclosure, the ammonia aqueous solution in the step (6) may be used in an amount of 0.5 equivalent or more, 1 equivalent or more, 1.5 equivalents or more, 2 equivalents or more, 2.5 equivalents or more or 3 equivalents or more, or 4 equivalents or less, 3.5 equivalents or less, 3 equivalents or less, 2.5 equivalents or less, 2 equivalents or less, 1.5 equivalents or less, 1 equivalent or less or 0.5 equivalent or less.

In an exemplary embodiment of the present disclosure, the step (6) may further include, after the step 1): 2) a step of stirring the resulting mixture solution. Specifically, in an exemplary embodiment of the present disclosure, the stirring in the step (6) may be performed for 5 minutes or longer, 10 minutes or longer, 20 minutes or longer, 30 minutes or longer, 40 minutes or longer, 50 minutes or longer, 60 minutes or longer or 70 minutes or longer, or for 70 minutes or shorter, 60 minutes or shorter, 50 minutes or shorter, 40 minutes or shorter, 30 minutes or shorter, 20 minutes or shorter or 10 minutes or shorter.

In an exemplary embodiment of the present disclosure, the step (6) may further include: 3) a step of filtering the resulting suspension.

In an exemplary embodiment of the present disclosure, the step (6) may further include: 4) a step of obtaining an R or S optical isomer of INT-3 by removing water from the filtered suspension, specifically under reduced pressure.

In another aspect, the present invention provides a method for manufacturing a compound of formula (IIIa) or (IIIb)

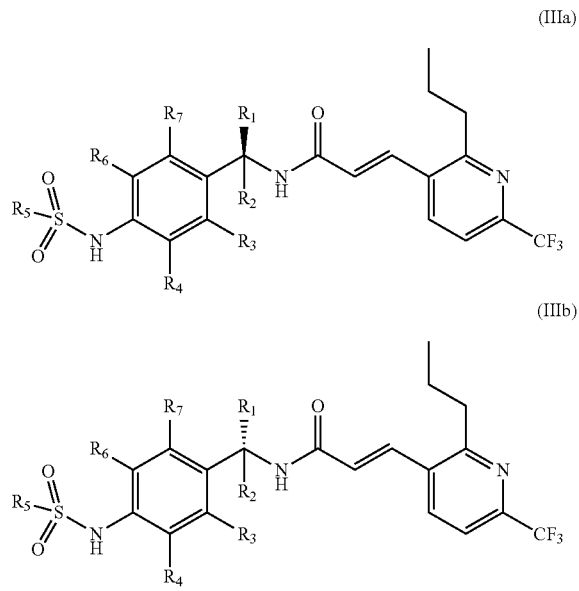

wherein, each of $R_1$, $R_2$, $R_3$, $R_4$, $R_5$, $R_6$ and $R_7$ is independently any one selected from a group consisting of H, $-NH_2$, a $C_{1-6}$ alkyl group, a $C_{2-6}$ alkenyl group, a $C_{2-6}$ alkynyl group and a halogen, and $R_1$ and $R_2$ are different from each other, comprising Resolving, specifically chiral resolving, the mixture of stereoisomers of the compound of formula (I) according to the method of present disclosure, and converting the resulting stereoisomer to the compound of formula (IIIa) or (IIIb). The converting step is described specifically also in Korean Patent Application No. 10-2009-700433.

In an exemplary embodiment of the present disclosure, the compound of formula (IIIa) may be (R)—N-[1-(3,5-difluoro-4-methanesulfonamino-phenyl)-ethyl]-3-(2-propyl-6-trifluoromethyl-pyridine-3-yl)-acrylamide and the compound of formula (I) may be N-{4-[(1R/S)-1-aminoethyl]-2,6-difluorophenyl}methanesulfonamide.

In another exemplary embodiment of the present disclosure, the converting step may comprise a step of coupling N-{4-[(1R)-1-aminoethyl]-2,6-difluorophenyl}methanesulfonamide (INT-3) with 3-(2-propyl-6-trifluoromethyl-pyridine-3-yl)-acrylic acid (INT-7).

The R isomer compound resolved by the method according to the present disclosure may be reacted with the substance described in Korean Patent Application No. 10-2009-700433 to be used as an intermediate to prepare the novel drug described in the patent application. Accordingly, in another aspect, the present disclosure relates to a method for preparing the novel drug described in Korean Patent Application No. 10-2009-700433 using the R isomer compound resolved by the method according to the present disclosure or the novel drug prepared by the method.

In an exemplary embodiment of the present disclosure, (R)—N-[1-(3,5-difluoro-4-methanesulfonylaminophenyl)-ethyl]-3-(2-propyl-6-trifluoromethyl-pridin-3-yl)-acrylamide obtainable by the method of the present disclosure with at least of 96%, at least of 97%, at least of 98%, at least of 99%, or 96%-99% of enantiomeric access is provided.

In another aspect, the present disclosure provides a TRPV1 antagonist containing (R)—N-[1-(3,5-difluoro-4-methanesulfonylaminophenyl)-ethyl]-3-(2-propyl-6-trifluoromethylpridin-3-yl)-acrylamide (PAC-14028) which is prepared by the method according to the present disclosure as an effective ingredient. The TRPV1 antagonist may be used in a pharmaceutical composition for preventing or treating the diseases described below.

In a further aspect, the present disclosure relates to a pharmaceutical composition containing (R)—N-[1-(3,5-difluoro-4-methanesulfonylaminophenyl)-ethyl]-3-(2-propyl-6-trifluoromethylpyridin-3-yl)-acrylamide, an optical isomer thereof or a pharmaceutically acceptable salt thereof and a pharmaceutically acceptable carrier, for preventing or treating a disease associated with the pathological stimulation and/or aberrant expression of the vanilloid receptor selected from a group consisting of pain, inflammatory disease of the joints, neuropathy, HIV-related neuropathy, nerve injury, neurodegeneration, stroke, urinary incontinence, cystitis, stomach/duodenal ulcer, irritable bowel syndrome (IBS) and inflammatory bowel disease (IBD), fecal urgency, gastroesophageal reflux disease (GERD), Crohn's disease, asthma, chronic obstructive pulmonary disease, cough, neurotic/allergic/inflammatory skin disease, psoriasis, pruritus, prurigo, skin irritation, inflammation of eye or mucous membrane, hyperacusis, tinnitus, vestibular hypersensitivity, episodic vertigo, myocardial ischemia, hirsutism, depilation, alopecia, rhinitis and pancreatitis.

In an exemplary embodiment of this aspect of the present disclosure, the pain may be or be associated with a disease selected from a group consisting of osteoarthritis, rheumatoid arthritis, ankylosing spondylitis, diabetic neuropathic pain, post-operative pain, toothache, fibromyalgia, myofascial pain syndrome, back pain, migraine and other types of headache.

In another aspect, the present disclosure provides a composition comprising: a chiral auxiliary which is one or more selected from the group consisting of 2,3-dibenzoyl-tartaric acid, O,O'-di-p-toluoyl-tartaric acid, a stereoisomer thereof, and a combination thereof; and a salt-forming compound which is one or more selected from the group consisting of mandelic acid, camphorsulfonic acid, a stereoisomer thereof, and a combination thereof. In an aspect, the composition may be a chiral resolving composition or a chiral resolving agent.

In an exemplary embodiment of the composition according to the present invention, the molar equivalent ratio of the chiral auxiliary to 1 molar equivalent of a mixture of stereoisomers which is to be resolved may be equal to or less than 0.5, or 0.15-0.5, 0.25-0.35, or 0.25.

In an exemplary embodiment of the composition according to the present invention, the molar equivalent ratio of the salt-forming compound to 1 molar equivalent a mixture of stereoisomers which is to be resolved may be 0.75-1.5.

In an exemplary embodiment of the present invention, the molar equivalent ratio of the salt forming compound to 1 molar equivalent of the chiral auxiliary in the composition may be between 1.5 and 6, specifically between 3 and 6 (i.e. 3 to 6 moles of the salt-forming compound for each mole of the chiral auxiliary).

In another aspect, the present disclosure provides a composition containing: a chiral auxiliary; and a salt-forming compound.

In an exemplary embodiment of the present disclosure, the composition may contain 0.10-0.5 equivalent of the chiral auxiliary per 1 equivalent of a mixture of stereoisomers which is desired to be chirally resolved.

In an exemplary embodiment of the present disclosure, the composition may contain 0.75-1.5 equivalent of the salt-forming compound per 1 equivalent of the mixture of stereoisomers.

In another aspect, the present disclosure provides a resolving kit comprising a chiral auxiliary; and a salt-forming compound.

In another aspect, the present disclosure provides a chiral resolving kit, comprising: a chiral auxiliary which is one or more selected from the group consisting of 2,3-dibenzoyltartaric acid, O,O'-di-p-toluoyl-tartaric acid, a stereoisomer thereof, and a combination thereof; and a salt-forming compound which is one or more selected from the group consisting of mandelic acid, camphorsulfonic acid, a stereoisomer thereof, and a combination thereof.

In an exemplary embodiment of the present disclosure, the chiral resolving kit according the present invention may further comprise written instructions for using the chiral auxiliary and the salt-forming compound, specifically for resolving a mixture of stereoisomers of a compound of formula (I).

In an exemplary embodiment of the present invention, the molar equivalent ratio of the chiral auxiliary to 1 equivalent of a mixture of stereoisomers which is to be resolved may be equal to or less than 0.5, 0.15-0.5, 0.25-0.35, or 0.25.

In an exemplary embodiment of the present invention, the molar equivalent ratio of the salt-forming compound to 1 equivalent of a mixture of stereoisomers which is to be resolved may be 0.75-1.5.

In an exemplary embodiment of the present disclosure, the kit according the present invention may further comprise written instructions for using the chiral auxiliary and the salt-forming compound.

In an exemplary embodiment of the present disclosure, the written instructions may contain instructions that the chiral auxiliary is used in amount of 0.10-0.5 equivalent per 1 equivalent of the mixture of stereoisomers which is desired to be chirally resolved.

In an exemplary embodiment of the present disclosure, the written instructions may contain instructions that the salt-forming compound is used in amount of 0.75-1.5 equivalent per 1 equivalent of the mixture of stereoisomers which is desired to be chirally resolved.

In an exemplary embodiment of the chiral resolving kit according to the present invention, the molar equivalent ratio of the salt forming compound to 1 molar equivalent of the chiral auxiliary may be between 1.5 and 6, specifically between 3 and 6 (i.e. 3 to 6 moles of the salt-forming compound for each mole of the chiral auxiliary).

In an exemplary embodiment of the present disclosure, the written instructions may contain instructions that the chiral auxiliary and the salt-forming compound are mixed with the mixture of stereoisomers in a polar protic solvent.

In an exemplary embodiment of the present disclosure, the written instructions may contain instructions about the method for resolving the mixture of stereoisomers described in the present disclosure.

In another aspect, the present disclosure provides a use of the composition or the kit according to present disclosure for chiral resolving of a mixture of stereoisomers.

Hereinafter, the present disclosure will be described in detail through the following examples. However, the following examples are for illustrative purposes only, and the scope of the present disclosure is not limited by these examples. Also, it will be apparent to those of ordinary skill in the art that various changes and modifications may be made thereto without departing from the scope of the present disclosure.

[Comparative Test Example 1] Measurement of Optical Purity for Existing Asymmetric Synthesis Method Asymmetric synthesis was performed according to Scheme 2.

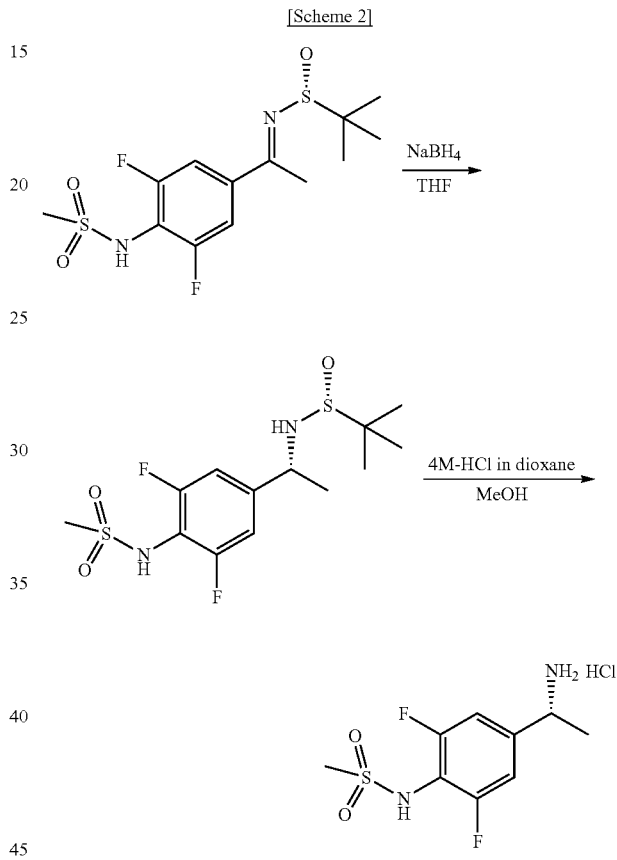

N-{2,6-Difluoro-4-[1-(2-methylpropane-2-sulfinylimino)-ethyl]-phenyl}-methanesulfonamide (1 equivalent) was dissolved by adding tetrahydrofuran (THF) (20 mL) in an amount of 10 times based on its weight. After further dissolving NaBH$_4$ (4 equivalents) in the resulting solution, reaction was performed for 10 hours at the temperatures described in Table 1. Then, CH$_3$OH was added dropwise until no hydrogen gas evolution was observed.

The mixture was concentrated under reduced pressure and then purified by chromatography to obtain N-{2,6-difluoro-4-[1-(2-methylpropane-2-sulfinylamino)-ethyl]-phenyl}-methanesulfonamide. The mixture was stirred at room temperature for 30 minutes while adding excess 4 M HCl in dioxane dropwise and then concentrated under reduced pressure. The resulting residue was purified by recrystallization in acetone to obtain (R)—N-[4-(1-aminoethyl)-2,6-difluorophenyl]-methanesulfonamide hydrochloride.

Enantiomeric excess (ee %) of the obtained salt was measured in the same manner as in the Test Example. The result is given in Table 1.

TABLE 1

| Comparative Example | Temperature during addition of NaBH₄ (° C.) | ee % (R isomer) |
|---|---|---|
| 1-1 | −48 | 96.2 |
| 1-2 | −30 | 95.4 |
| 1-3 | −20 | 95.2 |
| 1-4 | −10 | 94.9 |
| 1-5 | 0 | 94.2 |

As seen from Table 1, to achieve optical activity of 96% or higher with the existing method, the temperature should be maintained below −40° C. continuously for 10 hours, whereas the same optical activity can be achieved through stirring and purification at 50° C. according to the present disclosure. Accordingly, it can be seen that the method of the present disclosure is remarkably economical as compared to the existing method. If the reaction is extended to the plant scale, it will be much easier to maintain temperature at 50° C. than at −40° C. for 10 hours. Accordingly, the reaction scale of the method of the present disclosure can be more easily extended as compared to the existing method.

In addition, the existing method using 2-4 equivalents of sodium borohydride is very dangerous because explosive hydrogen is generated in excess and also heat is generated during the reaction. In contrast, the method of the present disclosure allows for preparation of commercially useful stereoisomers with optical activity of 96% or more without involving the excessive generation of explosive hydrogen or heat.

To conclude, the method of the present disclosure is more economical and safe as compared to the existing method.

[Comparative Test Example 2] Measurement of Optical Purity for Resolution Using One Chiral Resolving Agent N-[4-(1-Aminoethyl)-2,6-difluorophenyl]-methanesulfonamide (mixture of R and S stereoisomers) was prepared according to the preparation method described in Bioorganic & Medicinal Chemistry 15(18), 6043-6053; 2007. 1 equivalent of the prepared N-[4-(1-aminoethyl)-2,6-difluorophenyl]-methanesulfonamide was mixed with 1 equivalent of the chiral auxiliary described in Tables 2 and 3. To the resulting mixture was added a solvent (different solvents as described in the tables) of 10 times (vol.) based on the weight of the N-[4-(1-aminoethyl)-2,6-difluorophenyl]-methanesulfonamide. The resulting mixture solution was refluxed at 50° C. for 3 hours and then cooled to 25° C. The resulting solid was filtered using a Büchner funnel to obtain each N-[4-(1-aminoethyl)-2,6-difluorophenyl]-methanesulfonamide chiral acid salt. The obtained salt is a once-resolved salt.

The obtained once-resolved N-[4-(1-aminoethyl)-2,6-difluorophenyl]-methanesulfonamide salt was subjected to the above-described procedure of refluxing after adding the solvent of 10 times based on weight, cooling and then filtering for 1 and 2 times to obtain twice-resolved and thrice-resolved N-[4-(1-aminoethyl)-2,6-difluorophenyl]-methanesulfonamide salts.

After adding to each of the obtained N-[4-(1-aminoethyl)-2,6-difluorophenyl]-methanesulfonamide chiral acid salts water of 5 times based on its weight and 2 equivalents of a 28 vol % ammonia aqueous solution, the mixture was stirred for 30 minutes. The resulting suspension was filtered using a Büchner funnel and excess water was removed under reduced pressure to obtain N-[4-[(1R)-1-aminoethyl]-2,6-difluorophenyl]-methanesulfonamide or N-[4-[(1 S)-1-aminoethyl]-2,6-difluorophenyl]-methanesulfonamide (INT-3).

The optical purity (enantiomeric excess) of the obtained INT-3 was analyzed using a chiral HPLC column (Shiseido Chiral CD-Ph, 4.6 mm×250 mm, 5 μm). A mixture solution of 0.5 mol/L sodium perchlorate and methanol (75 vol %:25 vol %) was used as a mobile phase and the optical purity (enantiomeric excess, ee %) of each chiral acid salt was measured using the Waters e2695 Alliance HPLC system and calculated according to Equation 1. And, the yield of reaction was calculated according to Equation 2. The yield was calculated only for the thrice-resolved salt with the highest optical activity.

The result is given in Tables 2 and 3.

<HPLC Condition>
1. Column temperature=35° C.
2. Flow rate=0.5 mL/min
3. Detection wavelength=220 nm
4. $R_t$ (min)=20.4 (R-enantiomer %), 18.9 (S-enantiomer %)

Enantiomeric excess (% ee)=([Desired isomer]−[Opposite isomer])/([Desired isomer]+[Opposite isomer])×100  [Equation 1]

Yield (%)=(Actual yield/Theoretical yield)×100%  [Equation 2]

Actual yield: the amount of obtained product.
Theoretical yield: the maximum amount of product that can be obtained from the given amount of reactant.

TABLE 2

| | | | % ee (R enantiomer) | | | Yield of thrice- |
| Comp. Ex. | Chiral auxiliary | Solvent | Once-resolved | Twice-resolved | Thrice-resolved | resolved salt |
|---|---|---|---|---|---|---|
| 2-1 | (+)-2,3-Dibenzoyl-D-tartaric acid | Water (H₂O) | 40.1 | 77.5 | 91 | 15 |
| 2-2 | | Methanol | 68.4 | 84.2 | 97 | 9 |
| 2-3 | | Ethanol | 44.2 | 78.4 | 94 | 11 |
| 2-4 | | Isopropyl alcohol | 36.9 | 68.1 | 92.1 | 17 |
| 2-5 | | Butanol | 24.7 | 56.9 | 88.0 | 17 |

TABLE 3

| | | | % ee (R enantiomer) | | | Yield of thrice- |
| Comp. Ex. | Chiral auxiliary | Solvent | Once-resolved | Twice-resolved | Thrice-resolved | resolved salt |
|---|---|---|---|---|---|---|
| 3-1 | O,O'-Di-p-toluoyl-D-tartaric acid | Water (H₂O) | 38 | 71.5 | 75.4 | 16 |
| 3-2 | | Methanol | 63.2 | 79.2 | 96.1 | 4 |
| 3-3 | | Ethanol | 41.2 | 71.5 | 91 | 10 |
| 3-4 | | Isopropyl alcohol | 35.6 | 62.3 | 89.2 | 15 |
| 3-5 | | Butanol | 21.5 | 49.3 | 80.0 | 14 |

As can be seen from Tables 2 and 3, when only dibenzoyltartaric acid or ditoluoyltartaric acid was used, an optical isomer of higher purity could be obtained as the number of resolutions increased. In particular, the purity was the highest when methanol or ethanol was used. However, when the resolution was performed less than 3 times, the purity was very low as compared to a commercially useful purity of at least 96% ee.

In addition, the isomer yield was very low, such as below 20% when only dibenzoyltartaric acid or ditoluoyltartaric acid was used, regardless of the solvent.

[Test Example 1] Measurement of Optical Purity for Different Chiral Auxiliary and Auxiliary Salt-Forming Compound and Mixing Ratios Thereof N-[4-(1-Aminoethyl)-2,6-difluorophenyl]-methanesulfonamide (mixture of stereoisomers of R and S isomers) was prepared according to the preparation method described in Bioorganic & Medicinal Chemistry 15(18), 6043-6053; 2007. 1 equivalent of the prepared N-[4-(1-aminoethyl)-2,6-difluorophenyl]-methanesulfonamide was mixed with the chiral auxiliary and the auxiliary salt-forming compound described in Tables 4-8 of the equivalents described in the tables. To the resulting mixture was added a solvent (different solvents described in Tables 4-8) of 10 times based on the weight of the methanesulfonamide compound. The resulting mixture solution was refluxed at 50° C. for 3 hours and then cooled to 25° C. The resulting solid was filtered using a Büchner funnel to obtain each INT-3 chiral acid salt.

After adding to each of the obtained N-[4-(1-aminoethyl)-2,6-difluorophenyl]-methanesulfonamide chiral acid salts water of 5 times based on its weight and 2 equivalents of a 28 vol % ammonia aqueous solution, the mixture was stirred for 30 minutes. The resulting suspension was filtered using a Büchner funnel and excess water was removed under reduced pressure to obtain N-[4-[(1R)-1-aminoethyl]-2,6-difluorophenyl]-methanesulfonamide or N-[4-[(1 S)-1-aminoethyl]-2,6-difluorophenyl]-methanesulfonamide (INT-3).

The optical purity (enantiomeric excess) of the obtained INT-3 was analyzed using a chiral HPLC column (Shiseido Chiral CD-Ph, 4.6 mm×250 mm, 5 μm). A mixture solution of 0.5 mol/L sodium perchlorate and methanol (75 vol %:25 vol %) was used as a mobile phase and the optical purity (enantiomeric excess, ee %) of each chiral acid salt was measured using the Waters e2695 Alliance HPLC system.

The result is given in Tables 4-8. Table 4 shows the result of testing whether the optical purity and yield of INT-3 are affected by the optical activity of mandelic acid which is one of the auxiliary salt-forming compounds. Table 5 shows the result when 2,3-dibenzoyltartaric acid and mandelic acid were used. Table 6 shows the result when 2,3-dibenzoyltartaric acid and camphorsulfonic acid were used. Table 7 shows the result when di-p-toluoyltartaric acid and mandelic acid were used. Table 8 shows the result when ditoluoyltartaric acid and camphorsulfonic acid were used. Each table shows the result of obtaining the chiral acid salt using different solvents.

<HPLC Condition>
1. Column temperature=35° C.
2. Flow rate=0.5 mL/min
3. Detection wavelength=220 nm
4. $R_t$ (min)=20.4 (R-enantiomer %), 18.9 (S-enantiomer %)

The optical purity was calculated according to Equation 1, and the reaction yield was calculated according to Equation 2.

The camphorsulfonic acid, the mandelic acid, the 2,3-dibenzoyltartaric acid and the O,O'-di-p-toluoyltartaric acid used in the experiments were purchased from Sigma Aldrich.

TABLE 4

| | Combination of the chiral auxiliary and salt-forming compound (Equivalents) | | | | | |
|---|---|---|---|---|---|---|
| | (+)-2,3-Dibenzoyl-D-tartaric acid | Mandelic acid | | | | |
| Ex. | D | D | L | D + L (1:1) | Solvent | ee % (R isomer) | Yield (%) |
| Ex. 1-1 | 0.25 | 1.0 | | | Water | 88.0 | 41 |
| | | | | | Methanol | 99.3 | 16 |
| | | | | | Ethanol | 98.5 | 25 |
| | | | | | Isopropyl alcohol | 99.1 | 41 |
| Ex. 1-2 | 0.25 | | 1.0 | | Water | 88.1 | 40 |
| | | | | | Methanol | 99.4 | 15 |
| | | | | | Ethanol | 98.9 | 24 |
| | | | | | Isopropyl alcohol | 99.2 | 42 |
| Ex. 1-3 | 0.25 | | | 1.0 | Water | 88.2 | 41 |
| | | | | | Methanol | 99.4 | 17 |
| | | | | | Ethanol | 98.9 | 24 |
| | | | | | Isopropyl alcohol | 99.1 | 42 |

TABLE 5

| | Combination of the chiral auxiliary and salt-forming compound (Equivalents) | | | | |
|---|---|---|---|---|---|
| Ex. | (+)-2,3-dibenzoyl-D-tartaric acid | D/L-mandelic acid | Solvent | ee % (R isomer) | Yield (%) |
| 2-1 | 0.25 | 1 | Water | 88.2 | 40 |
| 2-2 | 0.35 | 1 | | 84.5 | 45 |
| 2-3 | 0.5 | 1 | | 56.3 | 21 |
| 2-4 | 1 | 1 | | 30 | 80 |
| 2-5 | 0.25 | 1 | Methanol | 99.4 | 15 |
| 2-6 | 0.35 | 1 | | 98.1 | 16 |
| 2-7 | 0.5 | 1 | | — | — |
| 2-8 | 1 | 1 | | — | — |
| 2-9 | 0.25 | 1 | Ethanol | 98.9 | 24 |
| 2-10 | 0.35 | 1 | | 98.1 | 25 |
| 2-11 | 0.5 | 1 | | 66.4 | 40 |
| 2-12 | 1 | 1 | | 10 | 71 |
| 2-13 | 0.25 | 1 | Isopropyl alcohol | 99.1 | 41 |
| 2-14 | 0.35 | 1 | | 98.7 | 42 |
| 2-15 | 0.5 | 1 | | 97.4 | 21 |
| 2-16 | 1 | 1 | | 15 | 82 |
| 2-17 | 0.25 | 0.75 | | 99.1 | 42 |
| 2-18 | 0.25 | 1.5 | | 99.2 | 38 |
| 2-19 | 0.35 | 0.75 | | 98.7 | 40 |
| 2-20 | 0.35 | 1.5 | | 98.6 | 32 |
| 2-21 | 0.5 | 0.75 | | 96.9 | 24 |
| 2-22 | 0.5 | 1.5 | | 96.1 | 16 |

*For mandelic acid, the same result was obtained for D and L isomers.

TABLE 6

| | Combination of the chiral auxiliary and salt-forming compound (Equivalents) | | | | |
|---|---|---|---|---|---|
| Ex. | (+)-2,3-Dibenzoyl-D-tartaric acid | (R,S)-10-Camphor-sulfonic acid | Solvent | ee % (R isomer) | Yield (%) |
| 3-1 | 0.25 | 1 | Water | 88.5 | 39 |
| 3-2 | 0.35 | 1 | | 84.7 | 42 |
| 3-3 | 0.5 | 1 | | 60.0 | 19 |
| 3-4 | 1 | 1 | | 32 | 75 |
| 3-5 | 0.25 | 1 | Methanol | 99.2 | 13 |

TABLE 6-continued

| Ex. | (+)-2,3-Dibenzoyl-D-tartaric acid | (R,S)-10-Camphorsulfonic acid | Solvent | ee % (R isomer) | Yield (%) |
|---|---|---|---|---|---|
| 3-6 | 0.35 | 1 | | 98.5 | 16 |
| 3-7 | 0.5 | 1 | | 97.3 | 9 |
| 3-8 | 1 | 1 | | — | — |
| 3-9 | 0.25 | 1 | Ethanol | 98.5 | 21 |
| 3-10 | 0.35 | 1 | | 98.5 | 24 |
| 3-11 | 0.5 | 1 | | 66.5 | 39 |
| 3-12 | 1 | 1 | | 15 | 68 |
| 3-13 | 0.25 | 1 | Isopropyl alcohol | 99.0 | 40 |
| 3-14 | 0.35 | 1 | | 98.9 | 41 |
| 3-15 | 0.5 | 1 | | 97.1 | 25 |
| 3-16 | 1 | 1 | | 16 | 81 |
| 3-17 | 0.25 | 0.75 | | 98.3 | 40 |
| 3-18 | 0.25 | 1 | | 98.8 | 38 |
| 3-19 | 0.25 | 1.5 | | 99.1 | 38 |
| 3-20 | 0.35 | 0.75 | | 97.1 | 41 |
| 3-21 | 0.35 | 1 | | 97.9 | 39 |
| 3-22 | 0.35 | 1.5 | | 98.7 | 34 |

*For camphorsulfonic acid, the same result was obtained for R and S isomers.

TABLE 7

| Ex. | (+)-O,O'-Di-p-toluoyl-D-tartaric acid | D/L-Mandelic acid | Solvent | ee % (R isomer) | Yield (%) |
|---|---|---|---|---|---|
| 4-1 | 0.25 | 1 | Water | 79.2 | 38 |
| 4-2 | 0.35 | 1 | | 75.3 | 41 |
| 4-3 | 0.5 | 1 | | 49.1 | 22 |
| 4-4 | 1 | 1 | | 21 | 79 |
| 4-5 | 0.25 | 1 | Methanol | 97.5 | 14 |
| 4-6 | 0.35 | 1 | | 96.2 | 15 |
| 4-7 | 0.5 | 1 | | — | — |
| 4-8 | 1 | 1 | | — | — |
| 4-9 | 0.25 | 1 | Ethanol | 97.1 | 21 |
| 4-10 | 0.35 | 1 | | 96.5 | 24 |
| 4-11 | 0.5 | 1 | | 56 | 39 |
| 4-12 | 1 | 1 | | 11 | 68 |
| 4-13 | 0.25 | 1 | Isopropyl alcohol | 98.1 | 38 |
| 4-14 | 0.35 | 1 | | 96.9 | 37 |
| 4-15 | 0.5 | 1 | | 96.1 | 21 |
| 4-16 | 1 | 1 | | 14 | 79 |
| 4-17 | 0.25 | 0.75 | | 98 | 40 |
| 4-18 | 0.25 | 1.5 | | 98.5 | 35 |
| 4-19 | 0.35 | 0.75 | | 96.5 | 39 |
| 4-20 | 0.35 | 1.5 | | 97 | 31 |
| 4-21 | 0.5 | 0.75 | | 96.1 | 24 |
| 4-22 | 0.5 | 1.5 | | 96.5 | 14 |

*For mandelic acid, the same result was obtained for D and L isomers.

TABLE 8

| Ex. | (+)-O,O'-Di-p-toluoyl-D-tartaric acid | (R,S)-10-Camphorsulfonic acid | Solvent | ee % (R isomer) | Yield (%) |
|---|---|---|---|---|---|
| 5-1 | 0.25 | 1 | Water | 79.0 | 35 |
| 5-2 | 0.35 | 1 | | 77.2 | 39 |
| 5-3 | 0.5 | 1 | | 51.2 | 20 |
| 5-4 | 1 | 1 | | 21.5 | 75 |
| 5-5 | 0.25 | 1 | Methanol | 98.1 | 16 |
| 5-6 | 0.35 | 1 | | 96.5 | 15 |
| 5-7 | 0.5 | 1 | | 97.0 | 8 |
| 5-8 | 1 | 1 | | — | — |
| 5-9 | 0.25 | 1 | Ethanol | 97.5 | 22 |
| 5-10 | 0.35 | 1 | | 96.1 | 23 |
| 5-11 | 0.5 | 1 | | 61 | 35 |
| 5-12 | 1 | 1 | | 13 | 71 |
| 5-13 | 0.25 | 1 | Isopropyl alcohol | 98.2 | 34 |
| 5-14 | 0.35 | 1 | | 97.0 | 35 |
| 5-15 | 0.5 | 1 | | 96.5 | 25 |
| 5-16 | 1 | 1 | | 17 | 75 |
| 5-17 | 0.25 | 0.75 | | 96.5 | 38 |
| 5-18 | 0.25 | 1 | | 97.1 | 35 |
| 5-19 | 0.25 | 1.5 | | 97.5 | 34 |
| 5-20 | 0.35 | 0.75 | | 96.5 | 39 |
| 5-21 | 0.35 | 1 | | 97.9 | 39 |
| 5-22 | 0.35 | 1.5 | | 97.1 | 34 |

*For camphorsulfonic acid, the same result was obtained for R and S isomers.

From Table 4, it can be seen that the optical activity of the mandelic acid which acts as a soluble salt-forming compound does not affect optical resolution. Specifically, almost the same result was obtained when D or L mandelic acid or a mixture thereof was used. Accordingly, it can be seen that the tartaric acid derivative such as dibenzoyltartaric acid plays an important role in optical resolution.

From Tables 5-8, it can be seen that, when diacyltartaric acid is used for the optical resolution, 2 equivalents (molecules) of N-[4-(1-aminoethyl)-phenyl]-methanesulfonamide and 1 equivalent (molecule) of diacyltartaric acid form a salt in a polar solvent such as water, methanol, ethanol and isopropyl alcohol, as described in Scheme 1.

Also, from Tables 5-8, it can be seen that, when diacyltartaric acid was used in an amount of 0.25 equivalent, 0.35 equivalent, 0.5 equivalent and 1 equivalent for given equivalents of mandelic acid and camphorsulfonic acid, the optical purity was highest when 0.25 equivalent was used, followed by 0.35 equivalent and 0.5 equivalent. When 1 equivalent of diacyltartaric acid was used, the optical purity was very low.

Accordingly, it can be seen that, in a polar solvent such as water, methanol, ethanol and isopropyl alcohol, 2 equivalents (molecules) of N-[4-(1-aminoethyl)-phenyl]-methanesulfonamide and 1 equivalent (molecule) of diacyltartaric acid form a salt which can be selectively resolved.

Specifically, referring to Table 5 and Table 6 wherein 2,3-dibenzoyl-D-tartaric acid and mandelic acid or camphorsulfonic acid were used, optical purity was low as 89% ee or lower when water was used as the solvent. When methanol or ethanol was used, the optical purity was 96% ee or higher when 0.25 equivalent or 0.35 equivalent of tartaric acid was used, but the yield was 25% or lower. However, the yield is 2 times or higher as compared to when only 2,3-dibenzoyl-D-tartaric acid was used (see Table 2). In particular, when the solvent was methanol and mandelic acid was used, the resolution did not occur when 0.5 equivalent of dibenzoyl-D-tartaric acid was used but the resolution did occur when camphorsulfonic acid was used. When the solvent was isopropyl alcohol, optical purity of 96% ee or higher could be obtained when 0.25 equivalent, 0.35 equivalent or 0.5 equivalent of tartaric acid was used and the yield was also 20% or higher. Particularly, when 0.25 equivalent or 0.35 equivalent of tartaric acid was used, the yield was 40% or higher.

Based on these results, experiment was performed in isopropyl alcohol with the equivalent of tartaric acid fixed while varying the equivalent of mandelic acid or camphorsulfonic acid (Examples 2-17 through 2-22 and Examples 3-17 through 3-22). As a result, when 0.5 equivalent or less of tartaric acid was used, the R isomer could be obtained with high optical purity of 96% ee or higher and high yield when 0.75-1.5 equivalent of mandelic acid or camphorsulfonic acid was used. In particular, the isomer could be obtained with high optical purity of 96% ee or higher and the highest yield of 42% in Example 2-17.

Referring to Tables 7 and 8 wherein O,O'-di-p-toluoyltartaric acid and mandelic acid or camphorsulfonic acid was used, optical purity was low as 80% ee or lower when water was used as the solvent. When methanol or ethanol was used, the optical purity was 96% ee or higher when 0.25 equivalent or 0.35 equivalent of tartaric acid was used, but the yield was 25% or lower. Yet, this yield is 2 times or higher as compared to when only O,O'-di-p-toluoyltartaric acid was used (see Table 3). In addition, the optical resolution did occur in methanol when camphorsulfonic acid was used, when 0.5 equivalent of di-p-toluoyltartaric acid was used. When the solvent was isopropyl alcohol, optical purity of 96% ee or higher could be obtained when 0.25 equivalent, 0.35 equivalent or 0.5 equivalent of tartaric acid was used and the yield was also 20% or higher. Particularly, when 0.25 equivalent or 0.35 equivalent of tartaric acid was used, the yield was 34% or higher.

In Examples 4-17 through 4-22 and Examples 5-17 through 5-22, experiment was performed in isopropyl alcohol with the equivalent of tartaric acid fixed while varying the equivalent of mandelic acid or camphorsulfonic acid. As a result, when 0.5 equivalent or less of tartaric acid was used, the R isomer could be obtained with high optical purity of 96% ee or higher and high yield when 0.75-1.5 equivalent of mandelic acid or camphorsulfonic acid was used. In particular, the isomer could be obtained with high optical purity of 96% ee or higher and the highest yield of 40% in Example 4-17.

To conclude, an R isomer with high optical purity of 96% ee or higher could be obtained when 0.25-0.5 equivalent of diacyltartaric acid and 0.75-1.5 equivalent of mandelic acid or camphorsulfonic acid were used. Especially, the isomer could be obtained with higher yield when the solvent was isopropyl alcohol. In addition, when the solvent was isopropyl alcohol, the isomer with high optical purity of 96% ee or higher could be obtained with a yield of 30% or higher by using 0.25-0.35 equivalent of diacyltartaric acid and 0.75-1.5 equivalent of mandelic acid or camphorsulfonic acid.

It will be obvious to those skilled in the art that N-{4-[(1S)-1-aminoethyl]-2,6-difluorophenyl}methanesulfonamide will be obtained when the 2,3-dibenzoyltartaric acid or the O,O'-di-p-toluoyltartaric acid is an L isomer.

Accordingly, an R or S optical isomer of high optical purity can be obtained by the method according to the present disclosure.

[Test Example 2] Preparation of (R)—N-[1-(3,5-difluoro-4-methanesulfonylaminophenyl)-ethyl]-3-(2-propyl-6-trifluoromethylpyridin-3-yl)-acrylamide

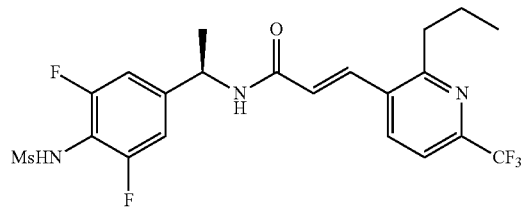

(R)—N-[1-(3,5-Difluoro-4-methanesulfonylaminophenyl)-ethyl]-3-(2-propyl-6-trifluoromethylpyridin-3-yl)-acrylamide was prepared using the N-{4-[(1R)-1-aminoethyl]-2,6-difluorophenyl}methanesulfonamide prepared according to the present disclosure, according to the method described in Korean Patent Application No. 10-2009-700433.

Specifically, N-{4-[(1R)-1-aminoethyl]-2,6-difluorophenyl} methanesulfonamide hydrochloride (62 mg, 0.22 mmol) was reacted with 3-(2-propyl-6-trifluoromethylpyridin-3-yl)-acrylic acid (56 mg, 0.22 mmol). The product was purified by crystallizing in ether to obtain the target compound (81 mg, 73%).

$^1$H NMR (300 MHz, DMSO-$d_6$): δ 9.50 (bs, 1H), 8.81 (d, 1H, J=7.8 Hz), 8.16 (d, 1H, J=8.4 Hz), 7.80 (d, 1H, J=7.8 Hz), 7.67 (d, 1H, J=15.6 Hz), 7.18 (d, 2H, J=7.2 Hz), 6.76 (d, 1H, J=15.6 Hz), 5.04 (m, 1H), 3.05 (s, 3H), 2.91 (m, 2H), 1.65 (m, 2H), 1.41 (d, 3H, J=6.9 Hz), 0.92 (t, 3H, J=7.2 Hz).

ESI [M+H]$^+$: 492.

Accordingly, the R isomer of the compound having a structure of formula (I), which has been resolved by the method according to the present disclosure, may be used as an intermediate to prepare various novel compounds that can act as TRPV1 antagonists using the substance or the method described in Korean Patent Application No. 10-2009-700433.

Hereinafter, formulation examples of the composition according to the present disclosure will be described. However, the following examples are for illustrative purposes only and it will be apparent to those of ordinary skill in the art that the scope of the present disclosure is not limited by the examples.

[Formulation Example 1] Amorphous Chiral Resolving Agent Compositions

An amorphous solid chiral resolving agent containing at least one of 0.15-0.5 equivalent of 2,3-dibenzoyltartaric acid and O,O'-di-p-toluoyltartaric acid; and at least one of 0.75-1.5 equivalent of mandelic acid and camphorsulfonic acid, per 1 equivalent of a mixture of stereoisomers.

[Formulation Example 2] Crystallized Chiral Resolving Agent Compositions

A crystallized solid chiral resolving agent containing at least one of 0.15-0.5 equivalent of 2,3-dibenzoyltartaric acid and O,O'-di-p-toluoyltartaric acid; and at least one of 0.75-1.5 equivalent of mandelic acid and camphorsulfonic acid, per 1 equivalent of a mixture of stereoisomers.

The invention claimed is:

1. A method for chiral resolution of a mixture of stereoisomers of a compound of formula (I),

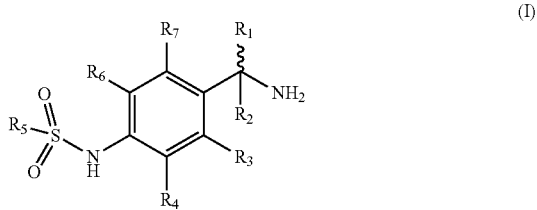

wherein each of $R_1$, $R_2$, $R_3$, $R_4$, $R_5$, $R_6$ and $R_7$ is independently any one selected from a group consisting of H, —$NH_2$, a $C_{1-6}$ alkyl group, a $C_{2-6}$ alkenyl group, a $C_{2-6}$ alkynyl group and a halogen, and $R_1$ and $R_2$ are different from each other, comprising mixing said mixture of stereoisomers of the compound of formula (I) with
(i) a chiral auxiliary; and
(ii) an auxiliary salt-forming compound
in the presence of a solvent, thereby precipitating a diastereomeric salt of said chiral auxiliary (i) with the compound of formula (I) in enantiomeric excess,
wherein the chiral auxiliary is one or more selected from a group consisting of 2,3-dibenzoyltartaric acid, O,O'-di-p-toluoyltartaric acid, a stereoisomer thereof, and a combination thereof, and the auxiliary sal-forming compound is one or more selected from a group consisting of mandelic acid, camphorsulfonic acid, a stereoisomer thereof, and a combination thereof.

2. The method according to claim 1, wherein the chiral auxiliary is one or more selected from a group consisting of 2,3-dibenzoyltartaric acid, O,O'-di-p-toluoyltartaric acid, a stereoisomer thereof, and a combination thereof and the auxiliary salt-forming compound is one or more selected from a group consisting of mandelic acid, camphorsulfonic acid, a stereoisomer thereof, and a combination thereof.

3. The method according to claim 1, wherein $R_2$ is hydrogen and an S enantiomer of the compound of formula (I) is obtained in enantiomeric excess when the chiral auxiliary is selected from a group consisting of the (−)-2,3-dibenzoyl-L-tartaric acid, (−)-O,O'-di-p-toluoyl-L-tartaric acid and a combination thereof.

4. The method according to claim 1, wherein the auxiliary salt-forming compound is D-mandelic acid, L-mandelic acid, (1R)-(−)-10-camphorsulfonic acid, (1S)-(+)-10-camphorsulfonic acid or a combination thereof.

5. The method according to claim 1, wherein the halogen is one or more selected from a group consisting of F, Cl, Br, and I.

6. The method according to claim 5, wherein $R_1$ is selected from a group consisting of methyl, ethyl, propyl, butyl and pentyl and $R_2$ is hydrogen.

7. The method according to claim 6, wherein $R_1$ is methyl, $R_2$, $R_3$ and $R_7$ are hydrogen, and $R_4$, $R_5$ and $R_6$ are independently selected from a group consisting of F, Cl, methyl, ethyl, and propyl.

8. The method according to claim 7, wherein the compound of formula (I) is N-{4-[(1R/S)-1-aminoethyl]-2,6-difluorophenyl}methanesulfonamide.

9. The method according to claim 1, wherein the solvent is one or more selected from a group consisting of water, a $C_{1-14}$ alcohol, acetic acid, nitromethane, propionic acid, formic acid and a combination thereof.

10. The method according to claim 9, wherein the solvent is one or more selected from a group consisting of water, methanol, ethanol and isopropyl alcohol.

11. The method according to claim 10, wherein the solvent is methanol, isopropyl alcohol or a combination thereof.

12. The method according to claim 1, wherein the solvent is added at an amount to achieve complete dissolution of all reactants.

13. The method according to claim 12, wherein the solvent is added at an amount of 5-15 times (v/w) of based on the total weight of the mixture of stereoisomers of the compound of formula (I).

14. The method according to claim 1, wherein the mixing is performed at 40-70° C. or at the boiling point of the solvent or solvent mixture.

15. The method according to claim 1, wherein the molar equivalent ratio of the chiral auxiliary to 1 molar equivalent of the mixture of stereoisomers is 0.10-0.5.

16. The method according to claim 15, wherein the molar equivalent ratio of the chiral auxiliary to 1 molar equivalent of the mixture of stereoisomers is 0.2-0.3.

17. The method according to claim 1, wherein the molar equivalent ratio of the auxiliary salt-forming compound to 1 molar equivalent of the mixture of stereoisomers is 0.5-1.5.

18. The method according to claim 17, wherein the molar equivalent ratio of the auxiliary salt-forming compound to 1 molar equivalent of the mixture of stereoisomers is 0.75-1.5.

19. The method according to claim 1, wherein the molar equivalent ratio of the chiral auxiliary and the auxiliary salt-forming compound together to 1 molar equivalent of the mixture of stereoisomers is 0.75-2.0.

20. A method for preparing a compound of formula (IIIa) or (IIIb)

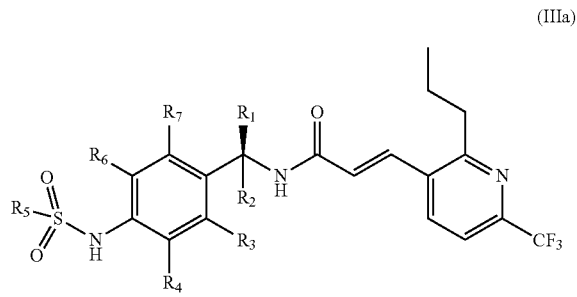

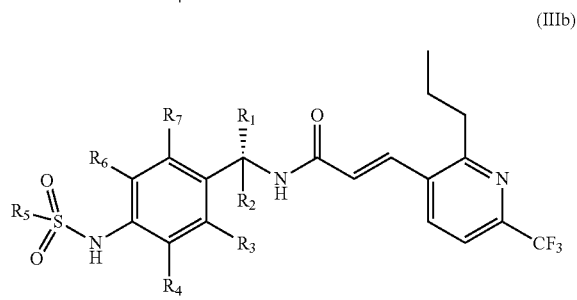

wherein, each of $R_1$, $R_2$, $R_3$, $R_4$, $R_5$, $R_6$ and $R_7$ is independently any one selected from a group consisting of H, —$NH_2$, a $C_{1-6}$ alkyl group, a $C_{2-6}$ alkenyl group, a $C_{2-6}$ alkynyl group and a halogen, and $R_1$ and $R_2$ are different from each other, comprising resolving the mixture of stereoisomers of the compound of formula (I) according to the method of claim 1, and converting the resulting stereoisomer to the compound of formula (IIIa) or (IIIb).

21. The method according to claim 20, wherein the compound of formula (IIIa) is (R)—N-[1-(3,5-difluoro-4-methanesulfonamino-phenyl)-ethyl]-3-(2-propyl-6-trifluoromethyl-pyridine-3-yl)-acrylamide and the compound of formula (I) is N-{4-[(1R/S)-1-aminoethyl]-2,6-difluorophenyl}methanesulfonamide.

22. The method according to claim 20, wherein said converting the resulting stereoisomer to the compound of formula (IIIa) or (IIIb) comprises coupling N-{4-[(1R)-1-aminoethyl]-2,6-difluorophenyl}methanesulfonamide (INT-3) with 3-(2-propyl-6-trifluoromethyl-pyridine-3-yl)-acrylic acid (INT-7).

* * * * *